US011655207B2

(12) United States Patent
Cho et al.

(10) Patent No.: US 11,655,207 B2
(45) Date of Patent: May 23, 2023

(54) PHARMACEUTICALLY ACCEPTABLE SALT OF ALKYLCARBAMOYL NAPHTHALENYLOXY OCTENOYLHYDROXY AMIDE OR OF DERIVATIVE THEREOF AND METHOD FOR PREPARING SAME

(71) Applicant: CRYSTALGENOMICS, INC., Gyeonggi-do (KR)

(72) Inventors: Jae Pyoung Cho, Gyeonggi-do (KR); Yong Ho Jung, Gyeonggi-do (KR); Joong Myung Cho, Seoul (KR)

(73) Assignee: CRYSTALGENOMICS, INC., Gyeonggi-Do (KR)

( * ) Notice: Subject to any disclaimer, the term of this patent is extended or adjusted under 35 U.S.C. 154(b) by 0 days.

(21) Appl. No.: 16/616,547

(22) PCT Filed: Apr. 18, 2018

(86) PCT No.: PCT/KR2018/004466
§ 371 (c)(1),
(2) Date: Nov. 25, 2019

(87) PCT Pub. No.: WO2018/230829
PCT Pub. Date: Dec. 20, 2018

(65) Prior Publication Data
US 2020/0283371 A1    Sep. 10, 2020

(30) Foreign Application Priority Data

Jun. 15, 2017  (KR) ........................ 10-2017-0075872

(51) Int. Cl.
*C07C 233/40* (2006.01)
*C07C 231/12* (2006.01)

(52) U.S. Cl.
CPC .......... *C07C 233/40* (2013.01); *C07C 231/12* (2013.01)

(58) Field of Classification Search
None
See application file for complete search history.

(56) References Cited

U.S. PATENT DOCUMENTS

| 5,073,376 A | 12/1991 | Kohl et al. |
| 7,696,374 B2 | 4/2010 | Abouabdellah et al. |
| 2009/0156674 A1 | 6/2009 | Macher et al. |
| 2010/0069630 A1 | 3/2010 | Lee et al. |
| 2010/0323988 A1 | 12/2010 | Wu et al. |
| 2011/0207769 A1 | 8/2011 | Catena Ruiz et al. |

FOREIGN PATENT DOCUMENTS

| CA | 2628040 A1 | 5/2007 |
| CN | 101107224 A | 1/2008 |
| CN | 101300226 A | 11/2008 |
| CN | 101573327 A | 11/2009 |
| EP | 2913322 A2 | 9/2015 |
| JP | 4-128223 A | 4/1992 |
| JP | 2008-528530 A | 7/2008 |
| JP | 2009-513697 A | 4/2009 |
| JP | 2010-502610 A | 1/2010 |
| JP | 2010-509208 A | 3/2010 |
| JP | 2011-504890 A | 2/2011 |
| KR | 10-0696139 B1 | 3/2007 |
| KR | 10-0711944 B1 | 5/2007 |
| KR | 10-2007-0101284 A | 10/2007 |
| KR | 10-0814092 B1 | 3/2008 |
| KR | 10-0814100 B1 | 3/2008 |
| KR | 10-2011-0096028 A | 8/2011 |
| KR | 10-1388596 B1 | 4/2014 |
| RU | 2400472 C2 | 9/2010 |
| RU | 2401256 C2 | 10/2010 |
| WO | 2006-079535 A1 | 8/2006 |
| WO | 2007-052938 A1 | 5/2007 |
| WO | 2008-054154 A1 | 5/2008 |
| WO | 2010-067980 A2 | 6/2010 |

OTHER PUBLICATIONS

Wiedmann et al., Pharmaceutical salts: Theory, used in solid dosage forms and in situ preparation in an aerosol. Asian Journal of Pharmaceutical Sciences, 2016, 11, 722-734.*
Crystallization and Precipitation. (2016). Retrieved from https://www.mt.com/us/en/home/applications/L1_AutoChem_Applications/L2_Crystallization.html#publications.*
Tala, Satishkumar. (2012). Re: How to make a salt of a novel compound?. Retrieved from: https://www.researchgate.net/post/How_to_make_a_salt_of_a_novel_compound2/5055c397e24a461b02000022/citation/download.*
Chemical Abstract Registry No. 2173017-02-0, indexed in the Registry File on STN CAS Online Feb. 7, 2018.*
Hwang et al., "A Novel Histone Deacetylase Inhibitor, CG0006, Induces Cell Death Through Both Extrinsic and Intrinsic Apoptotic Pathways", Anti-Cancer Drugs, vol. 20, No. 9, p. 815-821, (2009).
International Search Report for Application No. PCT/KR2018/004466 dated Jul. 26, 2018.
Office Action from copending Korean Application No. 10-2017-0075872 dated Apr. 19, 2018.
Office Action from copending Australian Application No. 2018283472 dated Mar. 13, 2020.

(Continued)

*Primary Examiner* — Po-Chih Chen
(74) *Attorney, Agent, or Firm* — Knobbe, Martens, Olson & Bear, LLP (57) ABSTRACT

The present invention relates to a pharmaceutically acceptable salt of alkylcarbamoyl naphthalenyloxy octenoylhydroxyamide or of a derivative thereof and a method for preparing same, and can improve moisture stability while maintaining the characteristics, such as the efficacy and effective dose, of a pharmaceutically acceptable salt of alkylcarbamoyl naphthalenyloxy octenoylhydroxyamide or of a derivative thereof. In addition, the present invention can simplify the production and manufacturing process of a formulation by improving hygroscopicity.

14 Claims, 5 Drawing Sheets

(56) References Cited

OTHER PUBLICATIONS

Office Action from copending Russian Application No. 2019144047 dated May 29, 2020.
Lee et al, "Histone deacetylase inhibitor, CG200745, attenuates cardiac hypertrophy and fibrosis in DOCA-induced hypertensive rats", Korean J Physiol Pharmacol, vol. 20 No. 5, p. 477-485, (2016).
Ono, "Analysis of Salt Selection of Current Active Pharmaceutical Ingredients", The Archives of Practical Pharmacy, vol. 73 No. 3, p. 176-182, (2013) (English Abstract Only).
Office Action from corresponding Japanese Patent Application No. 2019-569941 dated Feb. 2, 2021.
Office Action from corresponding Canadian Patent Application No. 3,066,601, based on PCT/KR2018/004466, dated Mar. 1, 2021.
Search Report from corresponding European Patent Application No. 18818326.3, based on PCT/KR2018/004466, dated Feb. 9, 2021.
International Search Report and Written Opinion from PCT/KR2018/004466, dated Jul. 26, 2018.

* cited by examiner

Fig. 1

(a) Foam (b) powder (c) gel-like

PHARMACEUTICALLY ACCEPTABLE SALT OF ALKYLCARBAMOYL NAPHTHALENYLOXY OCTENOYLHYDROXY AMIDE OR OF DERIVATIVE THEREOF AND METHOD FOR PREPARING SAME

CROSS REFERENCE TO RELATED APPLICATIONS

This application is a National Stage filing of PCT Application No. PCT/KR2018/004466 filed Apr. 18, 2018, entitled "PHARMACEUTICALLY ACCEPTABLE SALT OF ALKYLCARBAMOYL NAPHTHALENYLOXY OCTENOYLHYDROXYAMIDE OR OF DERIVATIVE THEREOF AND METHOD FOR PREPARING SAME", which claims priority to Korean Patent Application No. 10-2017-0075872 filed Jun. 15, 2017.

BACKGROUND OF THE INVENTION

1. Field of the Invention

The present invention relates to a pharmaceutically acceptable salt of alkylcarbamoyl naphthalenyloxy octenoyl hydroxyamide or a derivative thereof and a method for producing the same, in particular to a compound in the form of a salt capable of improving physicochemical stability and a method for producing the same.

2. Description of the Related Art

Histones are basic proteins that bind to DNA in the nucleus of eukaryotic cells and undergo reversible acetylation of the amino groups of lysine residues at specific positions in each molecule of histones. The acetylation of histones is related to the formation of higher structures of the chromatin or the cell division cycle, and thus it is involved in the regulation of the expression of genetic information and it is stably regulated by histone acetyltransferases (HATs) and histone deacetylases (HDACs). It is known that these enzymes neutralize positive charges of lysine residues (four residues for H4) at the amino terminus of histones by acetylation to induce transcriptional activity, or deacetylate them to give charge again to inhibit transcription, thereby inducing equilibrium of acetylation levels of histones and regulating gene expression in the phase of transcription.

HDAC has recently been found to play a role in promoting cell proliferation by being highly expressed in poor environmental conditions such as hypoxia, low glucose and cell carcinogenesis to inhibit expression of cell proliferation inhibitors. Therefore, it has been recognized as an important factor in regulating carcinogenicity and differentiation of cells. In other words, if high acetylation of chromatin inhibits cell proliferation and promotes differentiation, HDAC plays a crucial role in inducing cell proliferation through deacetylation of histones. This is supported by the fact that treatment of HDAC inhibitors results in inhibition of cell proliferation and angiogenesis. There is a need for the development of more selective and potent HDAC inhibitors. Accordingly, the possibility of alkylcarbamoyl naphthalenyloxy octenoyl hydroxyamide as an HDAC inhibitor has been confirmed, and research on this is ongoing.

However, such alkylcarbamoyl naphthalenyloxy octenoyl hydroxyamide has a property of absorbing moisture in the air, and thus there is a concern that a problem occurs that is vulnerable to physical and chemical stability. In order to solve this problem, it is necessary to go through several additional purification processes to remove related substances caused by the property of absorbing moisture, which may increase the production cost. In the case of the free base, it is difficult to maintain in a solid state due to hygroscopicity, which makes it difficult to mass-produce it. Therefore, there is a disadvantage in that a means such as a separate freezing storage device or packaging is further required.

Therefore, there is a need for a study on alkylcarbamoyl naphthalenyloxy octenoyl hydroxyamide as a physicochemically stable HDAC inhibitor.

SUMMARY OF THE INVENTION

It is an object of the present invention to provide a pharmaceutically acceptable salt of alkylcarbamoyl naphthalenyloxy octenoyl hydroxyamide or a derivative thereof.

It is other object of the present invention to provide a method for producing the salt.

It is another object of the present invention to provide a pharmaceutical composition for an anticancer agent comprising the salt as an active ingredient.

In order to solve the above problems, the present invention provides a pharmaceutically acceptable salt of alkylcarbamoylnaphthalenyloxy octenoyl hydroxyamide of the following formula (1) or a derivative thereof:

[Formula 1]

wherein, $R_1$ is $C_{1-3}$ alkyl which is unsubstituted or substituted by one or more substituent selected from the group consisting of halophenyl, $C_{1-3}$ alkoxy, $C_{1-3}$ alkoxy $C_{1-3}$ alkyl, cyclohexanyl, furanyl, thiophenyl, imidazole, imidazolidyl $C_{1-3}$ alkyl, $C_{1-3}$ alkylamino, di-$C_{1-3}$ alkylamino, hydroxylphenyl, teterahydrofuranyl, cyclohexyl, cyclohexenyl, oxopyrrolidinyl, $C_{1-3}$ alkoxyphenyl, di-$C_{1-3}$ alkylaminophenyl, $C_{1-3}$ alkylpyrrolidinyl and trifluromethoxyphenyl; pyrollidine unsubstituted or substituted by $C_{3-8}$ cycloalkyl, $C_{3-8}$ cycloalkyl $C_{1-3}$ alkyl, benzyl, $C_{1-3}$ alkyl or $C_{3-8}$ cycloalkylcarbonyl; piperidine substituted by $C_{1-3}$ alkyl or $C_{3-8}$ cycloalkyl; furan; or $C_{3-8}$ cycloalkyl, with the proviso that unsubstituted $C_{1-2}$ alkyl and $C_{1-2}$ alkyl substituted by $C_{1-2}$ alkylpyrrolidinyl are excluded, wherein the salt is selected from a phosphoric acid salt, a tartaric acid salt, a stearic acid salt, a gluconic acid salt, a fumaric acid salt, a naphthoic acid salt, 1-hydroxy-2-naphthoic acid salt and a mixture thereof.

Further, the present invention provides a method for producing a pharmaceutically acceptable salt of alkylcarbamoyl naphthalenyloxy octenoyl hydroxyamide or a derivative thereof, comprising the steps of:

1) adding an organic solvent to alkylcarbamoyl naphthalenyloxy octenoyl hydroxyamide of the formula (1) or a derivative thereof to extract free base, and 2) adding an acidic substance to the free base solution, wherein the acidic substance is selected from a phosphoric acid, a tartaric acid, a stearic acid, a gluconic acid, a fumaric acid, a naphthoic acid, a 1-hydroxy-2-naphthoic acid and a combination thereof.

Further, the present invention provides a pharmaceutical composition for an anticancer agent comprising as an active ingredient the pharmaceutically acceptable salt of alkylcarbamoyl naphthalenyloxy octenoyl hydroxyamide of the formula (1) or a derivative thereof.

Other specific embodiments of the present invention are included in the following detailed description.

Effect of the Invention

According to the present invention, it is possible to improve stability against moisture while retaining properties such as drug efficacy and effective amount of the pharmaceutically acceptable salt of the alkylcarbamoyl naphthalenyloxy octenoyl hydroxyamide or a derivative thereof. In addition, by improving the hygroscopicity, it is possible to simplify processes of production and commercialization of the preparation.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

The term "pharmaceutically acceptable salt", as used herein may be described in combination with a "pharmaceutical salt", and which means any inorganic or organic compound formulation which can be a relatively non-toxic to a subject to be administered and have harmless effective action. In addition, it may mean any organic or inorganic compound formulation in that side effects resulting from the salt do not impair the efficacy of the drug, that does not cause serious irritation to the subject to which the compound is administered, and does not impair the biological activity and properties of the compound.

The pharmaceutical salt may include acid addition salts formed by acids which form non-toxic acid addition salts containing a pharmaceutically acceptable anion, for example inorganic acids such as hydrochloric acid, sulfuric acid, nitric acid, phosphoric acid, hydrobromic acid and hydroiodic acid, organic acids such as tartaric acid, formic acid, citric acid, acetic acid, trichloroacetic acid, trifluoroacetic acid, gluconic acid, benzoic acid, malonic acid, glyconic acid, lactic acid, fumaric acid, maleic acid, salicylic acid and succinic acid, sulfonic acid such as methanesulfonic acid, ethanesulfonic acid, benzenesulfonic acid, p-toluenesulfonic acid and naphthalen-2-sulfonic acid. For example, the pharmaceutically acceptable carboxylic acid salt includes metal salts or alkaline earth metal salts formed with lithium, sodium, potassium, calcium and magnesium, amino acid salts such as lysine, arginine and guanidine, organic salts such as dicyclohexylamine, N-methyl-D-glucamine, tris(hydroxymethyl)methylamine, diethanolamine, coline and triethylamine

Hereinafter, the pharmaceutically acceptable salts of alkylcarbamoyl naphthalenyloxy octenoyl hydroxyamide or a derivative thereof according to the embodiments of the present invention will be described in more detail.

Alkylcarbamoyl naphthalenyloxy octenoyl hydroxyamide or a derivative thereof has been confirmed to have a possibility as an inhibitor of histone deacetylase (HDAC) (Korean Patent Registration No. 0814092).

According to the present invention, it is possible to provide a pharmaceutical preparation in the form of a salt in which stability against moisture is improved while retaining properties such as drug efficacy and effective amount of alkylcarbamoyl naphthalenyloxy octenoyl hydroxyamide or a derivative thereof.

In order to solve the above-described problems, the present invention provides a pharmaceutically acceptable salt of alkylcarbamoyl naphthalenyloxy octenoyl hydroxyamide of the following formula (1) or a derivative thereof.

[Formula 1]

wherein, $R_1$ is $C_{1-3}$ alkyl which is unsubstituted or substituted by one or more substituent selected from the group consisting of halophenyl, $C_{1-3}$ alkoxy, $C_{1-3}$ alkoxy $C_{1-3}$ alkyl, cyclohexanyl, furanyl, thiophenyl, imidazole, imidazolidyl $C_{1-3}$ alkyl, $C_{1-3}$ alkylamino, di-$C_{1-3}$ alkylamino, hydroxylphenyl, teterahydrofuranyl, cyclohexyl, cyclohexenyl, oxopyrrolidinyl, $C_{1-3}$ alkoxyphenyl, di-$C_{1-3}$ alkylaminophenyl, $C_{1-3}$ alkylpyrrolidinyl and trifluromethoxyphenyl; pyrollidine unsubstituted or substituted by $C_{3-8}$ cycloalkyl, $C_{3-8}$ cycloalkyl $C_{1-3}$ alkyl, benzyl, $C_{1-3}$ alkyl or $C_{3-8}$ cycloalkylcarbonyl; piperidine substituted by $C_{1-3}$ alkyl or $C_{3-8}$ cycloalkyl; furan; or $C_{3-8}$ cycloalkyl, with the proviso that unsubstituted $C_{1-2}$ alkyl and $C_{1-2}$ alkyl substituted with $C_{1-2}$ alkylpyrrolidinyl are excluded, wherein the salt may be selected from a phosphoric acid salt, a tartaric acid salt, a stearic acid salt, a gluconic acid salt, a fumaric acid salt, a naphthoic acid salt, a 1-hydroxy-2-naphthoic acid salt and a mixture thereof.

According to one embodiment, the salt may be selected from a phosphoric acid salt, a tartaric acid salt and a mixture thereof, which have relatively high stability and water solubility, for example it may comprise a phosphoric acid salt.

The preferred derivatives of alkylcarbamoyl naphthalenyloxy octenoyl hydroxyamide of the following formula (1) may be selected from the group consisting of following compounds:

1) (E)-N1-(3-(1H-imidazol-1-yl)propyl)-N8-hydroxy-2-((naphthalen-1-yloxy)methyl)octenediamide,
2) (E)-N8-hydroxy-N1-(4-hydroxyphenethyl)-2-((naphthalen-1-yloxy)methyl)-2-octenediamide,
3) (E)-N1-(3-(dimethylamino)-2,2-dimethylpropyl)-N8-hydroxy-2-((naphthalen-1-yloxy)methyl)octenediamide,
4) (E)-N1-(2-(diisopropylamino)ethyl)-N8-hydroxy-2-((naphthalen-1-yloxy)methyl)octenediamide,
5) (E)-N8-hydroxy-N1-(1-methoxypropan-2-yl)-2-((naphthalen-1-yloxy)methyl)-2-octenediamide,
6) (E)-N8-hydroxy-N1-(4-methoxybenzyl)-2-((naphthalen-1-yloxy)methyl)-2-octenediamide,
7) (E)-N1-(4-fluorophenethyl)-N8-hydroxy-2-((naphthalen-1-yloxy)methyl)-2-octenediamide,
8) (E)-N8-hydroxy-2-((naphthalen-1-yloxy)methyl)-N1-(tetrahydrofuran-2-yl)methyl)-2-octenediamide,
9) (E)-N1-(2-cyclohexenylethyl)-N8-hydroxy-2-((naphthalen-1-yloxy)methyl)-2-octenediamide,
10) (E)-N8-hydroxy-2-((naphthalen-1-yloxy)methyl)-N1-(3-(2-oxopyrrolidin-1-yl)propyl)-2-octenediamide,
11) (E)-N1-(furan-2-ylmethyl)-N8-hydroxy-2-((naphthalen-1-yloxy)methyl)-2-octenediamide,
12) (E)-N1-(4-(dimethylamino)benzyl)-N8-hydroxy-2-((naphthalen-1-yloxy)methyl)-2-octenediamide,
13) (E)-N8-hydroxy-N1-(2-methoxyethyl)-2-((naphthalen-1-yloxy)methyl)-2-octenediamide,
14) (E)-N1-cyclohexyl-N8-hydroxy-2-((naphthalen-1-yloxy)methyl)-2-octenediamide,
15) (E)-N8-hydroxy-2-((naphthalen-1-yloxy)methyl)-N1-(thiophen-2-ylmethyl)-2-octenediamide,
16) (E)-N8-hydroxy-N1-(4-methoxyphenethyl)-2-((naphthalen-1-yloxy)methyl)-2-octenediamide,
17) (E)-N8-hydroxy-2-((naphthalen-1-yloxy)methyl)-N1-(4-(trifluoromethoxy)benzyl)-2-octenediamide,
18) (E)-N1-(1-(cyclohexylmethyl)pyrrolidin-3-yl)-N8-hydroxy-2-((naphthalen-1-yloxy)methyl)-2-octenediamide,
19) (E)-N1-(1-cyclopentylpiperidin-4-yl)-N8-hydroxy-2-((naphthalen-1-yloxy)methyl)-2-octenediamide,
20) (E)-N1-(1-benzylpyrrolidin-3-yl)-N8-hydroxy-2-((naphthalen-1-yloxy)methyl)-2-octenediamide,
21) (E)-N8-hydroxy-N1-(1-isopropylpyrrolidin-3-yl)-2-((naphthalen-1-yloxy)methyl)-2-octenediamide,
22) (E)-N1-(1-(cyclohexanecarbonyl)pyrrolidin-3-yl)-N8-hydroxy-2-((naphthalen-1-yloxy)methyl)-2-octenediamide,
23) (E)-3-(8-(hydroxyamino)-2-((naphthalen-1-yloxy)methyl)-8-oxo-2-octeneamido)pyrrolidin-1-carboxylic acid t-butyl ester,
24) (E)-N8-hydroxy-2-((naphthalen-1-yloxy)methyl)-N1-(pyrrolidin-3-yl)2-octenediamide,
25) (E)-N1-(1-cyclohexylpyrrolidin-3-yl)-N8-hydroxy-2-((naphthalen-2-yloxy)methyl)-2-octenediamide,
26) (E)-N1-(1-cyclopropylpyrrolidin-3-yl)-N8-hydroxy-2-((naphthalen-1-yloxy)methyl)-2-octenediamide,
27) (E)-N1-(1-cyclopropylpiperidin-4-yl)-N8-hydroxy-2-((naphthalen-1-yloxy)methyl)-2-octenediamide,
28) (E)-N1-(1-ethylpiperidin-4-yl)-N8-hydroxy-2-((naphthalen-1-yloxy)methyl)-2-octenediamide,
29) (E)-N1-(1-ethylpyrrolidin-3-yl)-N8-hydroxy-2-((naphthalen-1-yloxy)methyl)-2-octenediamide,
30) (E)-N8-hydroxy-N1-(2-(1-methylpyrrolidin-2-yl)ethyl)-2-((naphthalen-1-yloxy)methyl)-2-octenediamide and
31) (E)-N8-hydroxy-N1-(1-isopropylpiperidin-4-yl)-2-((naphthalen-1-yloxy)methyl)-2-octenediamide Further, the present invention provides a method for producing a pharmaceutically acceptable salt of alkylcarbamoyl naphthalenyloxy octenoyl hydroxyamide or a derivative thereof, comprising the steps of:

1) adding an organic solvent to alkylcarbamoyl naphthalenyloxy octenoyl hydroxyamide of the formula (1) or a derivative thereof to extract free base, and 2) adding an acidic substance to the free base solution, wherein the acidic substance is selected from a phosphoric acid, a tartaric acid, a stearic acid, a gluconic acid, a fumaric acid, a naphthoic acid, a 1-hydroxy-2-naphthoic acid and a combination thereof.

According to one embodiment, the alkylcarbamoyl naphthalenyloxy octenoyl hydroxyamide or a derivative thereof may be in a solid, gel or solution state, and the solution state may refer to a state completely dissolved in an organic solvent or a suspension state.

According to one embodiment, the organic solvent may be selected from methanol, ethanol, propanol, tetrahydrofuran, chloroform, N,N-dimethylformamide (DMF), dimethyl sulfoxide (DMSO), acetonitrile, ethyl acetate and a combination thereof, for example it may comprise methanol, ethanol, propanol, tetrahydrofuran, chloroform, N,N-dimethylformamide (DMF), dimethyl sulfoxide (DMSO) and a combination thereof, which have relatively high solubility.

According to one embodiment, the acidic substance may comprise a phosphoric acid, a tartaric acid and a combination thereof which have relatively high water solubility, for example it may comprise a phosphoric acid.

According to one embodiment, the method for producing a pharmaceutically acceptable salt of alkylcarbamoyl naphthalenyloxy octenoyl hydroxyamide or a derivative thereof may further comprise a step of additionally adding a solvent having lower solubility than that of the solvent of step 1). The solvent having lower solubility than that of the solvent of step 1) may be selected from alcohols including methanol, ethanol and propanol, teterahydrofuran, acetonitrile, acetone and a combination thereof. For example, an organic solvent is added to the free salt of alkylcarbamoylnaphthalenioxy octenoyl hydroxy amide or a derivative thereof, and then it is observed whether or not precipitation occurs, that is, whether a salt is formed. If necessary, a solvent having lower solubility than that of the added organic solvent may be further added to observe whether or not precipitation occurs. The addition of the solvent having low solubility may be repeated 2 to 5 times, for example 2 times to obtain a salt.

The pharmaceutically acceptable salt of alkylcarbamoyl naphthalenyloxy octenoyl hydroxyamide or a derivative thereof according to the present invention has a water content of less than 3% when stored at 20 to 25° C. and a humidity of 50% or less for 3 days, for example, 2% or less.

According to one embodiment, the compound of the present invention may have the amount of related substances to be produced of less than 5% when stored at 20 to 25° C. for 3 days, for example less than 1%, for example less than 0.5%, for example 0.05% or less. The related substance may refer to an impurity or a byproduct which can be produced in addition to the desired compound in the production process of the compound.

According to the present invention, it is possible to improve the stability of the preparation by providing alkylcarbamoyl naphthalenyloxy octenoyl hydroxyamide or a derivative thereof in the form of a pharmaceutically acceptable salt, thereby facilitating mass production of a pharmaceutical composition for an anticancer agent containing it as an active ingredient. Specifically, several additional purification processes necessary to prevent the generation of related substances caused by a property of absorbing moisture, can be simplified, so that the process can be economically proceeded. In addition, it is possible to supplement the problem that a cold storage or packaging technique is further required in order to maintain an unstable solidified state of the preparation at room temperature and to minimize contact with moisture.

Hereinafter, embodiments of the present invention will be described in detail so that those skilled in the art can easily carry out the present invention. The present invention may, however, be embodied in many different forms and should not be construed as limited to the embodiments set forth herein.

Preparation Example 1: Selection of Organic Solvent

The solubility of the alkylcarbamoyl naphthalenyloxy octenoyl hydroxyamide compound of formula (1) in each organic solvent was measured in order to select an appropriate organic solvent. For solubility test, each organic solvent is taken up to about 10 mL at room temperature and alkyl carbamoyl naphthalenyloxy octenoyl hydroxyamide is added to the degree of supersaturation. They are stirred for 2 hours, and then centrifuged at 10,000 rpm to take supernatant. It is diluted in methanol and the solubility in each organic solvent is measured by an HPLC test. The results are shown in Table 1 below.

TABLE 1

| Solvent | Solubility (20° C.; mg/mL) | Solubility (50° C.; mg/mL) |
|---|---|---|
| Methanol | >68.4 | — |
| Ethanol | >77.4 | — |
| 2-propanol | 73.8 | 77.3 |
| Propanol | >70.3 | — |
| 1-butanol | >58.8 | — |
| Ethyl acetate | 4.6 | 20.3 |
| Acetone | 43.3 | 43.7 |
| 1,4-dioxane | 72.3 | 72.3 |
| Acetonitrile | 6.1 | 16.5 |
| Tetrahydrofuran | >74.0 | — |
| Chloroform | >80.7 | — |
| Tert-butylmethyl ether | 0.8 | 0.8 |
| Methylene Ketone | 66.6 | 69.7 |
| Heptane | 0.0 | 0.0 |
| Butan-2-ol | 39.6 | 72.0 |
| N,N-dimethylformamide | >76.6 | — |
| Dimethyl sulfoxide | >70.6 | — |
| Toluene | 1.0 | 3.3 |

As shown in Table 1, it can be confirmed that the solubility of the alkylcarbamoyl naphthalenyloxy octenoyl hydroxyamide compound of formula (1) is relatively high when methanol, ethanol, propanol, tetrahydrofuran, chloroform, N,N-dimethylformamide (DMF) or dimethyl sulfoxide (DMSO) is used as an organic solvent. In addition, it can be confirmed that when it is dissolved in acetonitrile or ethyl acetate the solubility is relatively low and in the case of t-butyl methyl ether (TBME), heptane or toluene the compound is hardly dissolved therein.

Preparation Example 2: Salt Formation

Salt screening was performed to evaluate the possibility of salt formation for alkylcarbamoyl naphthalenyloxy octenoyl hydroxyamide compound of formula (1).

Each acidic substance as shown in Table 2 was completely dissolved in methanol, and then slowly added to a free salt of the alkylcarbamoyl naphthalenyloxy octenoyl hydroxyamide compound of formula (1), followed by sealing with nitrogen filling. This was stored at room temperature for 24 hours to observe the occurrence of precipitation, and if necessary, in the solubility test, a solvent with significantly low solubility for the compound of formula (1) was selected and further added, followed by observation of the occurrence of precipitation.

After adding the low solubility solvent, the observation of the occurrence of precipitation was repeated up to two times. Finally, the vacuum drying was carried out under reduced pressure, and then the stability was evaluated. The results are shown in Table 3 below.

TABLE 2

| Nd. | Chemical name |
|---|---|
| 1 | Naphthoic acid, 1-hydroxy-2 |
| 2 | Benzensulfonic acid |
| 3 | Phosphoric acid |
| 4 | Malonic acid |
| 5 | Maleic acid |
| 6 | Toluensulfonic acid, para |
| 7 | Methanensulfonic acid |
| 8 | Naphthalene-2-sulfonic acid |

TABLE 2-continued

| Nd. | Chemical name |
|---|---|
| 9 | Fumaric acid |
| 10 | Taratar acid, (+)-L |
| 11 | Ethanesulfonic acid |
| 12 | Benzoic acid |
| 13 | Gluconic acid, (D–) |
| 14 | Acetic acid |
| 15 | Succinic acid |
| 16 | Glutaric acid |
| 17 | Stearic acid |
| 18 | Hippuric acid |
| 19 | Hydrochloric acid |
| 20 | Citric acid |
| 21 | Sulfuric acid |
| 22 | Trifluoracetic acid |

TABLE 3

| No. | Chemical name | acid addition | low solubility solvent 1st addition | low solubility solvent 2nd addition |
|---|---|---|---|---|
| 1 | Naphthoic acid, 1-hydroxy-2 | X | X | ○ |
| 2 | Benzensulfonic acid | X | X | Δ |
| 3 | Phosphoric acid | ○ | — | — |
| 4 | Malonic acid | X | X | Δ |
| 5 | Maleic acid | X | X | Δ |
| 6 | Toluensulfonic acid, para | X | X | Δ |
| 7 | Methanensulionic acid | X | X | Δ |
| 8 | Naphthalene-2-sulionic acid | X | X | Δ |
| 9 | Fumaric acid | X | X | ○ |
| 10 | Taratar acid, (+) L | X | ○ | — |
| 11 | Ethanesulfonic acid | X | X | Δ |
| 12 | Benzoic acid | X | X | Δ |
| 13 | Gluconic acid, (D–) | X | ○ | — |
| 14 | Acetic acid | X | X | Δ |
| 15 | Succinic acid | X | X | Δ |
| 16 | Glutaric acid | X | Δ | — |
| 17 | Stearic acid | X | X | Δ |
| 18 | Hippuric acid | X | X | Δ |
| 19 | Hydrochloric acid | X | — | — |
| 20 | Citric acid | X | X | Δ |
| 21 | Sulfuric acid | X | Δ | — |
| 22 | Trifluoracetic acid | X | Δ | — |

○: Precipitation in clear solution or immediate precipitation
Δ: Suspension or gel
X: No precipitation As shown in Tables 2 and 3 above, it can be seen that when phosphoric acid is added to the free salt of alkylcarbamoyl naphthalenyloxy octenoyl hydroxyamide of formula (1), a precipitate is gradually generated, that is, a salt is formed at room temperature. In the case of tartaric acid and gluconic acid, precipitation occurs when the first addition of a low solubility solvent (antisolvent) occurs, and in the case of fumaric acid, naphthoic acid and 1-hydroxy-2-naphthoic acid, precipitation occurs when the second addition of a low solubility solvent occurs. In addition, in the case of other acids, a cloudy suspension or gel of high viscosity is produced.

Experimental Example 1: Change in Appearance at Room Temperature

In order to evaluate the change in appearance of the salts according to Preparation Example 2, the respective precipitates were collected by filtration and vacuum dried. In the case of the suspension and the gel, firstly it was vacuum dried under reduced pressure and secondly vacuum dried for 24 to 48 hours.

Figure 1:
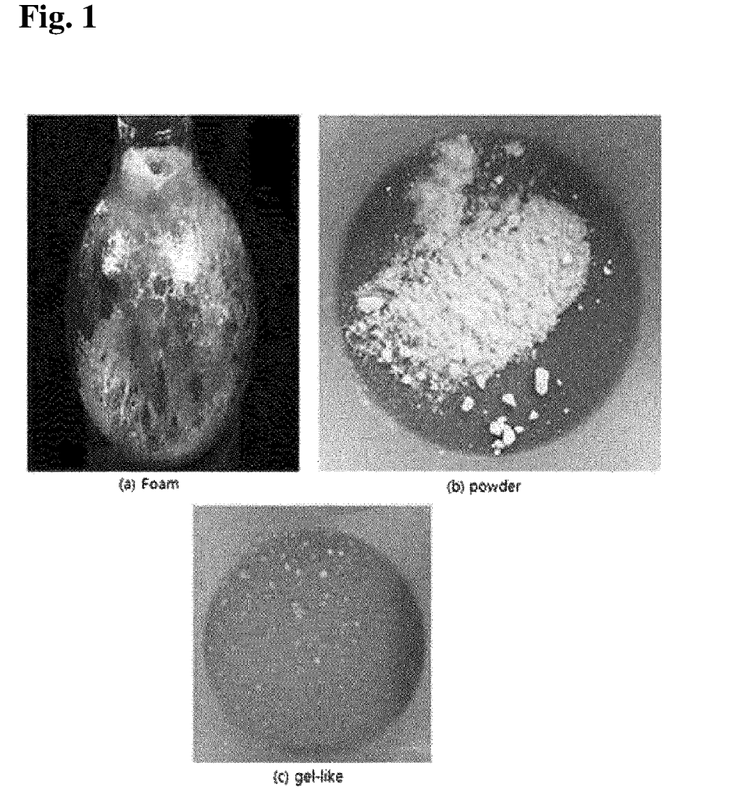
FIG. 1 is a photograph showing each property of the compound.

The dried material thus recovered was left at room temperature for 24 hours, and then the appearance of the compounds was observed. The results are shown in Table 4 below and photographs of the respective appearances are shown in FIG. 1 below.

TABLE 4

| Item | Salt | Initial appearance | Appearance (stored at R.T. for 24 hrs) |
|---|---|---|---|
|  | CG200745 free base | Foam | Gel-like |
| 1 | Naphthoic acid, 1-hydroxy-2 | Powder | Gel-like |
| 2 | Benzensulfonic acid | Foam | Gel-like |
| 3 | Phosphoric acid | Powder | Powder |
| 4 | Malonic acid | Foam | Gel-like |
| 5 | Maleic acid | Foam | Gel-1ike |
| 6 | Toluensulfonic acid, para | Foam | Gel-like |
| 7 | Methanensulfonic acid | Foam | Gel-like |
| 8 | Naphthalene-2-sulfonic acid | Powder | Gel-like |
| 9 | Fumaric acid | Powder | Gel-like |
| 10 | Taratar acid, (+)-L | Powder | Powder |
| 11 | Ethanesulfonic acid | Foam | Gel-like |
| 12 | Benzoic acid | Foam | Gel-like |
| 13 | Gluconic acid, (D–) | Powder | Gel-like |
| 14 | Acetic acid | Foam | Gel-like |
| 15 | Succinic acid | Powder | Gel-like |
| 16 | Glutaric acid | Powder | Gel-like |
| 17 | Stearic acid | Powder | Powder (Low water solubility) |
| 18 | Hippuric acid | Foam | Gel-like |
| 19 | Hydrochloric acid | Gel-like | Gel-like |
| 20 | Citric acid | Foam | Gel-like |
| 21 | Sulfuric acid | Gel-like | Gel-like |
| 22 | Trifluoracetic acid | Ge-1ike | Gel-like |

As shown in Table 4, in the case of phosphoric acid salt, tartaric acid salt, stearic acid salt, and the like, no change in appearance was observed.

Example: Preparation of Salt

[Formula 2]

Example 1: Preparation of Alkylcarbamoyl Naphthalenyloxy Octenoyl Hydroxyamide Tartaric Acid Salt NH$_2$OH HCl (0.75 g) is added to a 50 ml 3-neck flask, and anhydrous MeOH (7.5 ml, 0.01% or less of water content) is added and stirred at 10 to 20° C., and then cooled to −25 to −30° C. 30% NaOMe in MeOH (4.67 g, 12 equivalents) is added to the mixed solution while maintaining the temperature at −25 to −30° C. and stirred at the same temperature for 40 minutes. A compound of formula (2) (1 g), which is an intermediate, is added thereto and stirred at the same temperature for 2 hours. After the reaction is completed, an aqueous solution of 50% L-TTA (2.2 g) is slowly added at −20° C. or lower, and then purified water (12 ml) is added thereto while maintaining −10° C. and purified water (12 ml) is additionally added at 0° C. or lower. After adding DCM (7 ml) at room temperature and stirring for 5 minutes, the organic layer is separated and the water layer is taken. After repeated such washing operation three times, the water layer is cooled to 5° C., adjusted to pH 9.3 using a 25% aqueous solution of $Na_2CO_3$ (4 g), ethyl acetate (15 ml) is added and stirred for 5 minutes to extract. This operation is repeated four times to collect the organic solvent. A solution of 50% L-TTA (2 g) diluted with purified water (18 ml) is added to the separated organic layer, stirred for 5 minutes, and then the water layer is extracted (The temperature is maintained below 5° C. and the water layer is maintained at pH 3.5 ~4.0). 50% L-TTA (2.8 g) is added to the extracted water layer to adjust pH 2.5 ~2.8. The washed HP20 (23 g) is added to the extracted water layer and stirred at 0 to 5° C. for 1 hour to adsorb and then filtered. Excess washed HP20 (3 g) is charged to the bottom of the column tube and the adsorbed HP20 in the water layer is loaded and eluted with solvent under the conditions in the table below.

TABLE 5

| Flow rate | 25 ml/min | |
|---|---|---|
| Solvent temperature | 5 to 8° C. | |
| Solvent condition | 100% purified water | 12 min |
| | 5% ACN + 95% purified water | 15 min |
| | 10% ACN + 90% purified water | 15 min |
| | 30% ACN + 70% purified water | 15 min |

It is collected only effluent by 30% ACN in purified water and concentrated under reduced pressure below 30° C. to remove ACN. The concentrated solution was solidified using a freeze dryer to obtain CG0200745 TTA salt (Obtained: 520 mg, Yield: 48%, Purity: 99.57%).

Example 2: Preparation of Alkylcarbamoyl Naphthalenyloxy Octenoyl Hydroxyamide Phosphoric Acid Salt HO—$NH_2HCl$ (13.66 g, 196.58 mmol, 5 equivalents) is added to a reactor, MeOH (136.6 ml) is added and stirred, and then cooled to −25 to −30° C. NaOMe (30% in MeOH, 85.0 g, 472.01 mmol, 12 equivalents) is added while maintaining the temperature below −10° C. and cooled to −25 ~−30° C. and stirred for 40 minutes. A compound of formula (2) (18.2 g, 39.31 mmol), which is an intermediate, is added thereto and reacted for 2 to 3 hours while maintaining −20 to −25° C. After the reaction is completed, a 50% aqueous solution of L-tartaric acid (40.0 g) which was prepared in advance is added below −20° C., and then purified water (436.8 ml) is added thereto below 0° C. After dissolving below 5° C., the pH of the solution is adjusted to 6.5 to 7 while adding a 50% aqueous solution of L-tartaric acid (13.5 g) (After pH adjustment, discard TTA aqueous solution if left, and if not, prepare additionally). When the temperature rises to 15 ~20° C., the reaction solution is washed with MC (273 ml). After separating the layers, activated carbon SA-1500 (5.4 g) is added to the aqueous layer and stirred for 20 minutes. Activated carbon SA-1500 is filtered through a filter and washed with purified water. While adding a 25% aqueous solution of $Na_2CO_3$ (72.8 g) to the resulting aqueous solution, the pH of the aqueous solution is adjusted to 9.3 to 9.5. While maintaining the temperature at 15 to 20° C., MC (273 ml) is added to the aqueous solution to extract organic substances. The separated organic layer is cooled to 5 ~10° C. and then extracted with a $H_3PO_4$ aqueous solution (85% $H_3PO_4$, dissolved 4.53 g of $H_3PO_4$ in 72.8 ml of purified water). Acetone (491.4 ml) is added to the separated water layer, and the mixture was stirred at 15 to 20° C. for 1 hour. The precipitated crystals are filtered off and washed with acetone (36.4 ml). The wet was dried under reduced pressure for 6 hours below 30° C. to obtain a crude $H_3PO_4$ salt of CG200745 (Obtained: 11.77 g, Yield: 57.0%). The resulting salt compound is completely dissolved in purified water (58.8 ml), and then acetone (353 ml) is added and stirred at 15 to 20° C. for 1 hour. The precipitated crystals are filtered off and washed with acetone (36.4 ml). The wet was dried under reduced pressure for 6 hours below 30° C. to obtain a $H_3PO_4$ salt of CG200745 (Obtained: 10 g, Yield: 85.0%, HPLC purity: 99.5%, Less than 0.1% of each impurity).

Example 1-1: Preparation of a Lyophilized Injection of Alkylcarbamoyl Naphthalenyloxy Octenoyl Hydroxyamide Tartaric Acid Salt 120.0 g of alkylcarbamoyl naphthalenyloxy octenoyl hydroxyamide tartaric acid salt is added to 4.0 L of injection water with nitrogen bubbling for 15 minutes and dissolved with stirring at 400 rpm for 30 minutes. After filtration, the mixture is subdivided into 1 mL portions of sterile washed brown vials and lyophilized to prepare an injection (30 mg/vial). The injection of tartaric acid salt is stored in brown transparent glass vials with white to pale pinkish solids and can be dissolved in use.

Example 2-1: Preparation of a Lyophilized Injection of Alkylcarbamoyl Naphthalenyloxy Octenoyl Hydroxyamide Phosphoric Acid Salt 125.0 g and 250.0 g of alkylcarbamoyl naphthalenyloxy octenoyl hydroxyamide phosphoric acid salt is added to 4 L of injection water with nitrogen bubbling for 15 minutes, respectively, and dissolved with stirring at 400 rpm for 30 minutes. After filtration, the mixture is subdivided into 4 mL portions of sterile washed brown vials and lyophilized to prepare an injection (125 mg/vial and 250 mg/vial). The injection of phosphoric acid salt is stored in brown transparent glass vials with white to pale pinkish solids and can be dissolved in use.

Experimental Example: Evaluation of Stability

In order to evaluate stability of the compound according to the above Examples, as Comparative Example 1, each of the appearance, the water content and the amount of related substances was measured using the free salt of alkyl carbamoyl naphthalenyloxy octenoyl hydroxyamide of formula (1).

Stability evaluation includes observing the change with storage time in conditions of room temperature (20 to 25° C., 50% or less), long term (25±2° C. and 60±5% RH), acceleration (40±2° C. and 75±5% RH) and severe (60±2° C.).

Experimental Example 1: Evaluation of Change in Moisture Content

In order to evaluate the change in moisture content, the compounds according to Examples and Comparative Examples were stored in an open state at room temperature (20 to 25° C., 50% or less), and the change was measured by the difference between the initial moisture content and the moisture content after 3 days. The results are shown in FIG. 2 below.

Figure 2:
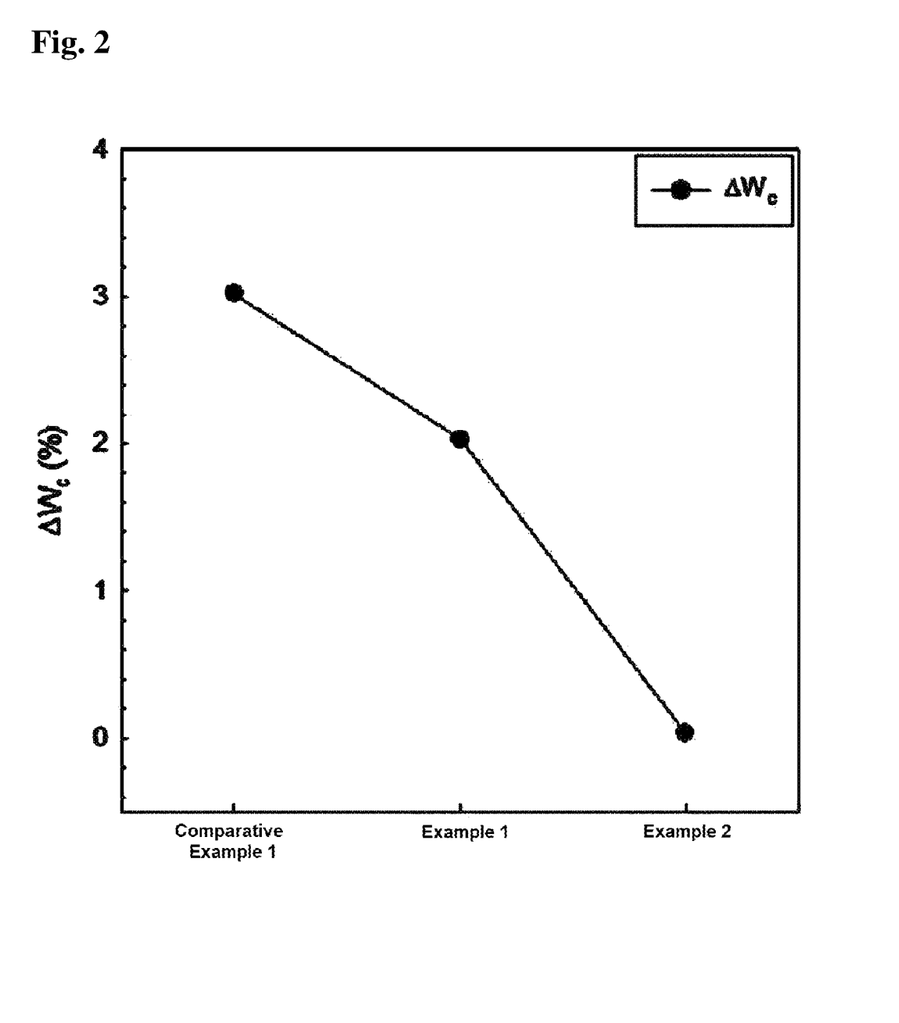
FIG. 2 is a graph showing changes in moisture content in Examples and Comparative Examples.

As shown in FIG. 2, in Comparative Example 1 the moisture content was increased by about 3%, in Example 1 the moisture content was increased by 2%, and in Example 2 the change in moisture content was about 0.01%, which is extremely small.

Experimental Example 2: Evaluation of Change in Appearance

In order to evaluate the change in appearance of the compounds according to Comparative Examples and Examples, it was observed after storing each compound in accordance with the conditions shown in Table 6 below.

TABLE 6

| Item | Storage period | Room temperature | Long-term | Acceler-ation | Severe |
| --- | --- | --- | --- | --- | --- |
| Comparative Example 1 | Initial value | | Foam | | |
| | 1 day | Gel-like | Gel-like | Gel-like | Gel-like |
| | 7 days | — | — | — | — |
| Example 1 | Initial value | | Powder | | |
| | 1 day | Powder | Gel-like | Gel-like | Powder |
| | 7 days | Powder | — | — | Powder Color changed (pale yellow) (reduced particle size) |
| Example 2 | Initial value | | Powder | | |
| | 1 day | Powder | Powder | Powder | Powder |
| | 7 days | Powder | Powder | Powder | Powder |

As shown in Table 6, it can be seen that in Comparative Example 1 moisture was absorbed and the appearance was changed from initial foam such as a sponge to a highly viscous liquid or gel structure after 1 day (24 hours), and in Example 2 the appearance remained constant regardless of the conditions.

Experimental Example 3: Evaluation of Change in Content

In order to evaluate the change in content of the compounds according to Examples, each compound was stored in an open state or in a polyethylene bottle package (added silica gel). The results measured in the open state are shown in Table 7 below, and the results measured in the bottle packaging state are shown in Table 8 below.

TABLE 7

| Item | Storage period | Room temperature | Long-term | Acceler-ation | Severe |
| --- | --- | --- | --- | --- | --- |
| Example 1 | Initial value | | 98.9 | | |
| | 1 day | 101.0 | 99.9 | 92.3 | 101.1 |
| | 3 days | 101.9 | N.T. | N.T. | 97.2 |
| | 7 days | 100.1 | N.T. | N.T. | 89.1 |
| Example 2 | Initial value | | 99.5 | | |
| | 1 day | 103.4 | 104.3 | 104.6 | 103.3 |
| | 3 days | 102.6 | 102.6 | 102.3 | 99.6 |
| | 7 days | 100.0 | 99.4 | 100.7 | 102.2 |

*N.T.: Test not performed due to the observation of change in appearance.

TABLE 8

| Item | Storage period | Room temperature | Long-term | Acceler-ation | Severe |
| --- | --- | --- | --- | --- | --- |
| Example 1 | Initial value | | 98.9 | | |
| | 1 day | 99.3 | 99.1 | 89.1 | 101.2 |
| | 3 days | 99.5 | 84.1 | 84.0 | N.T. |
| | 7 days | 99.4 | 78.5 | 78.5 | N.T. |
| Example 2 | Initial value | | 99.5 | | |
| | 1 day | 98.6 | 103.5 | 101.2 | 101.6 |
| | 3 days | 98.8 | 99.9 | 100.1 | 100.4 |
| | 7 days | 99.3 | 100.9 | 101.1 | 101.4 |

*N.T.: Test not performed due to the observation of change in appearance.

As shown in Tables 7 and 8, it can be seen that, in the case of Example 1, the content is maintained constant at room temperature regardless of the packaging state, and in the case of Example 2, the content is maintained constant without being affected by the packaging state, heat and humidity.

Figure 3:
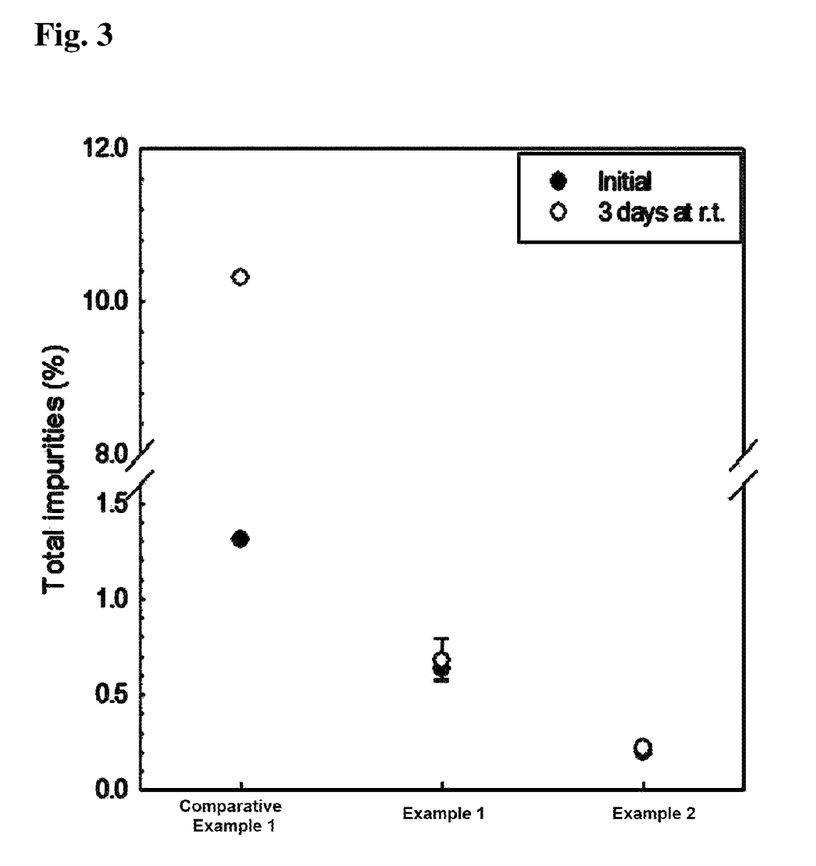
FIG. 3 is a graph showing changes in the amount of related substances to be produced in Examples and Comparative Examples.

Experimental Example 4: Evaluation of Change in the Amount of Related Substance In order to evaluate the change in the amount of related substances according to Comparative Examples and Examples, each compound was stored in an open state at room temperature for 3 days. The results are shown in FIG. 3. As shown in FIG. 3, in the case of Comparative Example 1, the amount of related substances are increased by about 10%, while in Example 1 the change is 0.05% and in Example 2 the change is 0.02%, indicating that the increase was relatively insignificant.

Figure 4:
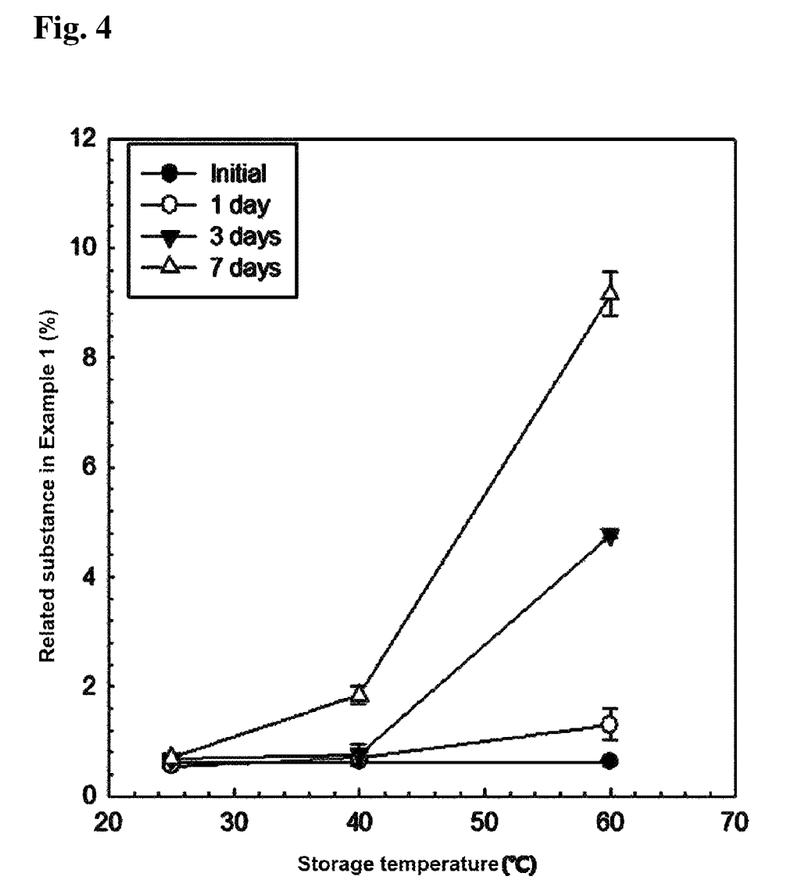
FIG. 4 is a graph showing changes in the amount of related substances to be produced in Example 1.
Figure 5:
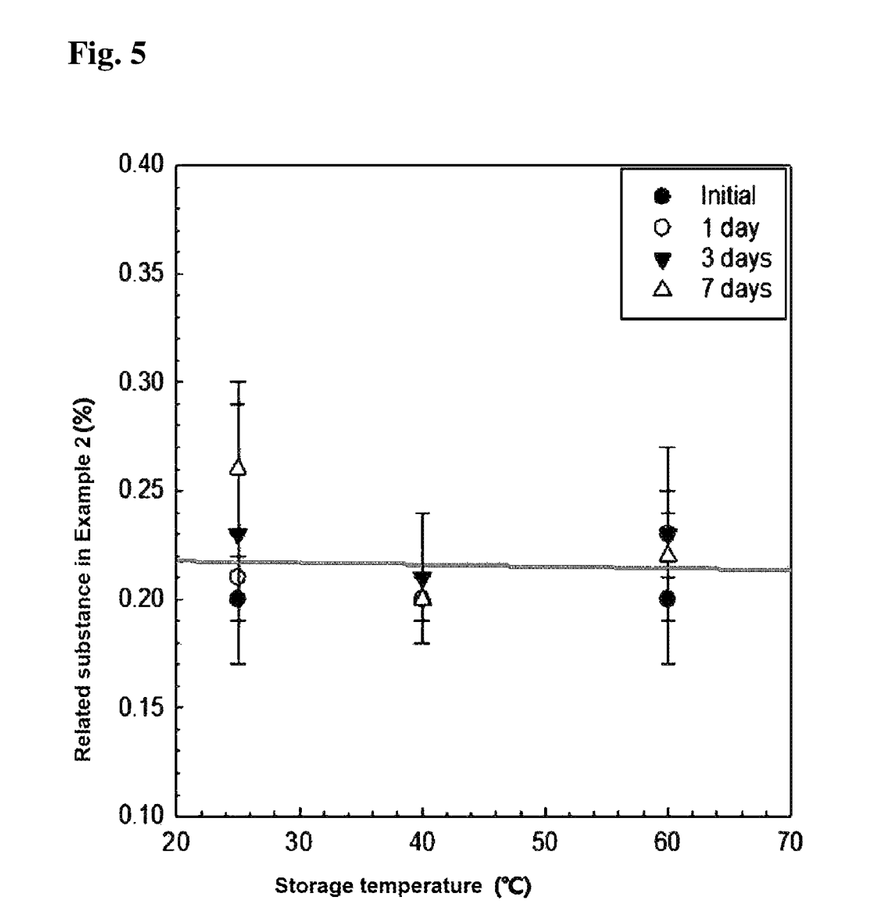
FIG. 5 is a graph showing changes in the amount of related substances to be produced in Example 2.

In addition, for the compounds according to Examples 1 and 2, the change in the amount of formation of the related substances according to temperature and storage period is shown in FIGS. 4 and 5 below. As shown in FIG. 4, in the case of Example 1, the amount of formation of the related substances was maintained in a certain range at a relatively low temperature. As shown in FIG. 5, in the case of Example 2, it can be seen that the amount of formation of the related substances is maintained uniformly in a certain range of about 0.22% without being affected by the storage temperature and period.

As can be seen from the results of the above experimental example, the pharmaceutical salt of alkylcarbamoyl naphthalenyloxy octenoyl hydroxyamide according to the present invention is confirmed to greatly improve the stability by minimizing the effects of storage conditions, temperature, humidity, etc.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A phosphoric acid salt of alkylcarbamoyl naphthalenyloxy octenoyl hydroxyamide of Formula 1:

[Formula 1]

Wherein $R_1$ is —$CH_2CH_2CH_2N(CH_3)_2$.

2. The phosphoric acid salt of alkylcarbamoyl naphthalenyloxy octenoyl hydroxyamide according to claim 1, wherein the phosphoric acid salt has a water content of less than 3% when stored at room temperature for 3 days.

3. The phosphoric acid salt of alkylcarbamoyl naphthalenyloxy octenoyl hydroxyamide according to claim 1, wherein the phosphoric acid salt has less than 3% impurities when stored at 20° C. to 30° C. for 3 days.

4. The phosphoric acid salt of alkylcarbamoyl naphthalenyloxy octenoyl hydroxyamide according to claim 1, wherein the phosphoric acid salt is in the form of a powder after storage at 20° C.-25° C. in a 50% or less relative humidity atmosphere for 1 day.

5. A pharmaceutical composition comprising the phosphoric acid salt of alkylcarbamoyl naphthalenyloxy octenoyl hydroxyamide according to claim 1.

6. A method for producing the phosphoric acid salt of alkylcarbamoyl naphthalenyloxy octenoyl hydroxyamide according to claim 1, comprising steps of:
1) forming a free base solution of the alkylcarbamoyl naphthalenyloxy octenoyl hydroxyamide of the Formula 1 in methanol; and
2) adding phosphoric acid to the free base solution;

[Formula 1]

wherein $R_1$ is —$CH_2CH_2CH_2N(CH_3)_2$.

7. The method according to claim 6, wherein the method further comprises a step of 3) additionally adding acetone to the free base solution.

8. The method according to claim 7, wherein the phosphoric acid is added as an aqueous solution.

9. The method according to claim 6, wherein the free base solution of the alkylcarbamoyl naphthalenyloxy octenoyl hydroxyamide of the Formula 1 is formed by reacting a compound of Formula 2 with $NH_2OH \cdot HCl$,

[Formula 2]

10. The method according to claim 9, wherein the method further comprises adding L-tartaric acid to the free base solution of the alkylcarbamoyl naphthalenyloxy octenoyl hydroxyamide of the Formula 1 prior to adding phosphoric acid.

11. A phosphoric acid salt of prepared by the method of claim 9.

12. The phosphoric acid salt of claim 11, wherein the free base solution of the alkylcarbamoyl naphthalenyloxy octenoyl hydroxyamide of the Formula 1 is formed by reacting the compound of Formula 2 with $NH_2OH \cdot HCl$ in the presence of NaOMe.

13. The phosphoric acid salt of claim 12, wherein the method further comprises adding L-tartaric acid to the free base solution of the alkylcarbamoyl naphthalenyloxy octenoyl hydroxyamide of the Formula 1 prior to adding phosphoric acid.

14. A pharmaceutical composition comprising the phosphoric acid salt of claim 11.

* * * * *